(12) United States Patent
Keil et al.

(10) Patent No.: US 9,968,715 B2
(45) Date of Patent: May 15, 2018

(54) METHOD FOR DEPOSITING COLOURED MARKERS MADE FROM TITANIUM OXIDES ON MEDICAL TECHNOLOGY PRODUCTS AND COATING SYSTEM FOR PRODUCING COATED MATERIALS

(71) Applicant: Fraunhofer-Gesellschaft Zur Förderung Der Angewandten Forschung E.V., München (DE)

(72) Inventors: Andreas Keil, Bremen (DE); Ralph Wilken, Rastede (DE); Jörg Ihde, Lilienthal (DE); Thomas Lukasczyk, Ritterhude (DE); Dirk Salz, Bremen (DE); Jost Degenhardt, Bremen (DE)

(73) Assignee: FRAUNHOFER-GESELLSCHAFT ZUR FORDERUNG DER ANGEWANDTEN, Munich (DE)

( * ) Notice: Subject to any disclaimer, the term of this patent is extended or adjusted under 35 U.S.C. 154(b) by 130 days.

(21) Appl. No.: 14/911,077

(22) PCT Filed: Aug. 1, 2014

(86) PCT No.: PCT/EP2014/066655
§ 371 (c)(1),
(2) Date: May 9, 2016

(87) PCT Pub. No.: WO2015/018767
PCT Pub. Date: Feb. 12, 2015

(65) Prior Publication Data
US 2016/0250389 A1   Sep. 1, 2016

(30) Foreign Application Priority Data
Aug. 9, 2013 (DE) .......... 10 2013 215 835

(51) Int. Cl.
| A61L 31/08 | (2006.01) |
| A61L 27/30 | (2006.01) |
| A61L 27/50 | (2006.01) |
| A61L 31/14 | (2006.01) |
| A61B 17/70 | (2006.01) |
| A61B 17/80 | (2006.01) |
| A61B 17/84 | (2006.01) |
| A61B 17/86 | (2006.01) |
| A61L 31/02 | (2006.01) |
| C23C 16/48 | (2006.01) |
| C23C 16/50 | (2006.01) |

(52) U.S. Cl.
CPC ........ *A61L 31/088* (2013.01); *A61B 17/7049* (2013.01); *A61B 17/80* (2013.01); *A61B 17/846* (2013.01); *A61B 17/848* (2013.01); *A61B 17/866* (2013.01); *A61L 27/306* (2013.01); *A61L 27/50* (2013.01); *A61L 31/022* (2013.01); *A61L 31/026* (2013.01); *A61L 31/14* (2013.01); *C23C 16/483* (2013.01); *C23C 16/50* (2013.01); *A61L 2420/02* (2013.01); *A61L 2420/04* (2013.01); *A61L 2430/02* (2013.01); *A61L 2430/38* (2013.01)

(58) Field of Classification Search
USPC ............ 427/255.11, 255.19, 255.21, 255.23, 427/255.28, 255.29, 255.36; 428/336, 428/472, 698, 701; 433/167, 173, 174; 623/11.11, 23.52
See application file for complete search history.

(56) References Cited

U.S. PATENT DOCUMENTS

| 6,465,042 | B2 * | 10/2002 | Saitoh .................. C23C 16/405 427/255.11 |
| 7,157,096 | B2 * | 1/2007 | Zhang ..................... A61L 27/32 424/423 |
| 7,524,791 | B2 * | 4/2009 | Furuya .................. B01J 35/004 427/255.36 |
| 7,547,471 | B2 * | 6/2009 | Bjursten ............... A61L 27/306 604/382 |
| 2001/0012567 | A1 | 8/2001 | Saitoh et al. |
| 2006/0161263 | A1 | 7/2006 | Sul |
| 2006/0194066 | A1 * | 8/2006 | Ye ........................ C03C 17/2456 428/701 |
| 2007/0202361 | A1 | 8/2007 | Frauchiger et al. |
| 2007/0275350 | A1 * | 11/2007 | Hall ...................... A61C 8/0012 433/173 |
| 2010/0092537 | A1 * | 4/2010 | Stromme ............... A61L 27/306 424/423 |

FOREIGN PATENT DOCUMENTS

| DE | 10 2009 023459 A1 | 12/2010 |
| EP | 0893513 A1 | 1/1999 |
| GB | 2455993 B | 9/2012 |
| WO | WO 2008/056323 A1 | 5/2008 |
| WO | WO 2009/091331 | 7/2009 |

OTHER PUBLICATIONS

Battiston et al "Dental Implants of Complex Form Coated by Nanostructured TiO2 Thin Films via MOCVD" Matl Sci. Forum, vol. 35 (2000) p. 151-157.*
Li et al "Visible-light Photodegradation of Rhodamine B on Carbon Doped Titanium Oxide thiin Film Prepared bt Atmospheric MOCVD" Adv. MAtl Res. vols. 26-28 (2007) p. 633-636.*

* cited by examiner

*Primary Examiner* — Archene Turner
(74) *Attorney, Agent, or Firm* — Preti Flaherty Beliveau & Pachios LLP

(57) ABSTRACT

The invention relates to medical technology products, for example a medical implant or a medical instrument, having colored markings based on titanium oxides, to the use of coatings based on titanium oxides for the production of coated materials, such as medical technology products, in particular for titanium oxide-based coating for the colored marking of the surface of medical technology products, and to a method for depositing colored markings based on titanium oxides on medical technology products.

23 Claims, No Drawings

METHOD FOR DEPOSITING COLOURED MARKERS MADE FROM TITANIUM OXIDES ON MEDICAL TECHNOLOGY PRODUCTS AND COATING SYSTEM FOR PRODUCING COATED MATERIALS

The invention relates to medical technology products, for example a medical implant or a medical instrument, having carbon-containing coatings as colored markings based on titanium oxides, to the use of corresponding coatings based on titanium oxides for the colored marking of the surface of medical technology products, and to a method for depositing colored markings based on titanium oxides on medical technology products.

The coating of materials, for example also of medical technology products, for the colored marking of the surface is known in the prior art, as are methods suitable for that purpose. For example, methods which produce titanium dioxide layers on surfaces by means of physical vapor deposition (PVD) or sputter deposition are known in patent documents WO 2009/091331 A1, US 2007/0202361 A1 and GB 2455993 A. Also known are methods which produce $TiO_2$ coatings by means of chemical vapor deposition (CVD) (e.g. GB 2455993 A; US 2007/0202361 A1). These methods are used, for example, in the coating/marking of medical bone implants in order to produce a bioactive, crystalline $TiO_2$ layer (WO 2009/091331 A1) or for the colored marking of medical implants or tools.

WO 2009/091331 A1 thus discloses a method for producing coated medical bone implants, comprising the steps of providing a substrate and depositing a bioactive crystalline $TiO_2$ coating by means of physical vapor deposition (PVD) at a temperature in the range of >50° C. and <800° C. The coated implants so obtained have an enhanced biomimetic reaction.

US 2007/0202361 A1, or WO 2006/002553 A1, discloses an interference-generating, colored coating for identifying and characterizing surgical implants and instruments. The coating is suitable both as a colored marking and as a diffusion barrier for such surgical implants and instruments. The coating is a biocompatible, transparent layer which is bonded to the surface of the implant or instrument, has a constant layer thickness and is not or is only slightly electrically conducting, that is to say is a dielectric. The coating is also suitable for generating interferences and interference colors over the entire visible spectrum.

GB 2455993 A also describes a coated product having at least one layer applied by means of a PVD method or a CVD method and at least one layer which has been applied by means of an ALD (atomic layer deposition) method. Further ALD and CVD/PVD layers can also be applied in different arrangements. The mentioned methods for depositing the coatings can be carried out in apparatuses having a vacuum chamber, which are suitable for carrying out both methods, ALD and CVD/PVD methods. The appearance of the coated products in terms of color is based on a transparent coating and color-giving particles or on a color shading due to surface plasmon resonance.

US 2001/012567 A, or EP 0893513 A1, discloses a material or substrate having a film of titanium dioxide with crystalline orientation, the preparation of which takes place with heating of the substrate to 300° C. or more. The material having titanium dioxide as a film with crystalline orientation is said to have antimicrobial activity, stain resistance and ultra-hydrophilic properties. It is intended for applications in the kitchen, such as cooking utensils, tableware, refrigerators, general healthcare devices, toilet materials or toilet rooms, filters for air conditioners, electronic components, building materials, and materials associated with roads.

The methods of the prior art still have a number of disadvantages. Physical vapor deposition (PVD) is carried out in this method as a low-pressure process in a vacuum chamber and therefore requires a very high technical and thus also financial outlay. The same is also true of sputter deposition, which is likewise a PVD process, where a sputter source is also necessary in addition to the already high outlay of the PVD process. Chemical vapor deposition (CVD) or metal organic chemical vapor deposition (MO-CVD) are for the mentioned purposes also low-pressure processes in a vacuum chamber. There are also a few processes which are carried out at atmospheric pressure, for example the methods already mentioned above, but the deposition in those cases is conventionally produced thermally by relatively intensive heating of the substrate.

Finally, there may be mentioned as a wet-chemical process also the sol-gel process, in which the chemical composition of the boundary surface with the substrate, the chemical composition and structure within the coating, the amount and size of titanium dioxide particle inclusions in the coating, the adhesion of the coating to the substrate, may be problematic with regard to a uniform and lasting quality of the coating. If the layer is to have adequate stability, post-tempering is essential or the achievable surface morphology at the boundary surface with the atmosphere may not satisfy practical requirements.

The methods of the prior art accordingly have a number of disadvantages, and there is a need for improved methods, in particular also industrial-suited methods, for producing high-quality coatings on surfaces of medical technology products, in particular, for example, on surfaces of medical implants or medical instruments.

Accordingly, the object underlying the invention is to overcome the disadvantages of the prior art and provide high-quality coatings, suitable for colored marking, for surfaces of medical technology products, in particular for surfaces of medical implants or medical instruments. The coatings are in particular to be obtainable with a low technical outlay as compared with those known from the prior art. The object is also to provide an improved, in particular industrial-suited method for producing high-quality coatings which are suitable for colored marking, and the use thereof in the production of medical products, especially implants or instruments, having colored marking on the surface.

The object is achieved by the medical implant or medical instrument specified in the claims, by the use specified in the claims of the coating thereby defined for the colored marking of the medical implant or medical instrument, and by the method specified in the claims for producing the medical implant or medical instrument having a coating for colored marking.

In order to achieve the object there is hereby proposed in particular a method for depositing titanium oxide layers, which appear colored owing to interference effects, for the marking of medical products, and a coating system for producing coated materials or substrates, in particular coated medical products. The layers to be applied according to the invention are preferably (owing to the chosen deposition process) partially or (almost) completely amorphous. The layers to be applied according to the invention are titanium oxide layers, wherein the expression "titanium oxide" includes all oxides of titanium within the meaning of this text, in particular also titanium dioxide.

The term "substrate" (or "material") is understood within the context of the present invention in the sense of the meaning customary in materials science of a material to be treated or a surface to be treated. The term "substrate" thus means a bottom layer or base layer in the sense of a carrier for another substance or another material, wherein the surface of the carrier, that is to say of the substrate, is enhanced or coated by the other substance or the other material. In the field of gas phase deposition coatings, for example CVD coatings, the substrate is accordingly the material on which a thin layer of another substance or another material is deposited. The material properties, but in particular the surface and the surface condition of the substrate, can be of great importance for the quality (e.g. adhesion) of the layer. For example, the substrate for the coating can be a steel alloy (e.g. tool steel) or titanium (e.g. in the case of implants) or also ceramics material or polymeric plastics material or combinations thereof, for example composite materials.

"Amorphous" within the meaning of this application means that the atomic building blocks are not arranged in crystal lattices. Unlike in a crystalline substance, in which there is both a short-range order between the building blocks (i.e. constant distances and angles relative to the closest neighboring atoms) and a long-range order (regular repetition of a motif in a crystal lattice), in the amorphous state there is only a more or less pronounced short-range order.

The diffraction of X-rays, electron beams and neutron beams at amorphous substances leads in the case of small diffraction angles to a small number of diffuse interference rings (halos), from the positions of which the preferred interatomic distances in the short-order range can be derived. Crystalline substances, on the other hand, produce a large number of sharp reflections.

The diffraction of visible light at thin layers leads to interference color phenomena in the case of both crystalline and amorphous materials. However, preference is given within the meaning of this invention to the (partially) amorphous and interference-capable layers which are preferably to be used according to the invention.

The method according to the invention, by means of which medical technology products coated in accordance with the invention, in particular medical implants or medical instruments (most particularly those which are intended and designed for contact with the human or animal body in particular during a surgical operation), are produced with a defined colored marking can also take the form of a process based on an atmospheric, chemical vapor deposition (CVD) and can be used for the color marking of a very wide variety of materials having reflective surfaces. The method according to the invention allows metal organic or organometallic titanium precursors to be used for the deposition of titanium oxide layers having defined layer thicknesses which, with suitable layer thicknesses, lead to interference color phenomena. By varying the absolute moisture in the environment of the coating nozzle, the chemistry of the starting materials used for the coating, the distance between the coating nozzle and the substrate, the process speed, the geometry of the coating nozzle, the change in the corresponding flows and the respective mixtures thereof, it is possible purposively to adjust the properties of the layers in terms of layer thickness and thus, for example, also interference color, homogeneity and content of $TiO_2$ particle inclusions.

The central point of the present invention is that the products according to the invention, or the products produced by the method according to the invention, have a proportion of carbon in the coating. Surprisingly, it has been found that, for the purposes of color marking, a certain proportion of carbon in the marking layer can be accepted. By purposively varying the carbon content, the mechanical properties, such as hardness, internal stresses in the layer, flexibility and also the layer adhesion can be adapted. In general, the hardness increases when the carbon content is reduced, while when the carbon content is increased, the flexibility of the coating also increases.

The fact that carbon may be present in small amounts in the marking coating allows the coating process to be designed to be technically uncomplicated: it is not necessary to work at low pressure, nor does the substrate have to be heated to a high temperature, such as, for example, more than 250° C., for the deposition process. Subsequent tempering steps for removing the proportion of carbon are also not absolutely necessary. In addition, it is possible to use carbon-containing precursors, which permit a deposition reaction which is particularly target-oriented and takes place under gentle conditions.

The embodiments and variants of the invention will be described in greater detail below with reference to characterizing features and parameters. The medical technology products according to the invention, in particular the medical implants or medical instruments, can hereby be identified by at least one of the following characterizing parameters or features: layer thickness; refractive index; chromaticity, for example in a defined color space; local delimitation of the layer; adhesion; type of substrate; material of the substrate; chemical composition, in particular titanium, oxygen and carbon content. Characterizing parameters or features of the method according to the invention are at least one of the following criteria: distance of the coating nozzle from the substrate; precursors by type and amount; amount of moisture; (inert) process carrier gas (e.g. nitrogen); vaporization temperature; type of coating apparatus, in particular, for example, nozzle used; relative proportions of the gases used (e.g. process gases/precursors to one another); preliminary cleaning/activation.

Accordingly, the invention relates to a medical implant or medical instrument comprising on its surface a colored marking in the form of a coating, wherein the coating comprises or consists of ≥85 at. %, preferably ≥90 at. %, particularly preferably ≥95 at. % and most particularly preferably ≥98 at. %, in each case based on the total number of all the atoms of the coating (as 100 at. %) without H (hydrogen), Ti (titanium) and O (oxygen) and C (carbon) and/or halides. However, it is preferred that, in a departure from the above, the amounts apply and halides are not included. Halides are desirable in particular when the method according to the invention is so changed that halogen-containing titanium compounds are used as the layer formers (precursors). XPS, X-ray photoelectron spectroscopy, is suitable for measuring the number (amount) of each of the elements Ti, O, C and/or halide, in each case given as at. % based on the total number of all the atoms of the coating (as 100 at. %), and the total number of all the atoms of the coating. Unless indicated otherwise, the at. % values are therefore to be understood in the following as "measured by means of XPS". Hydrogen H is not taken into consideration in the total number of all the atoms of the coating since any H present is not detected by this method. In order to be able to determine the chemical composition of the actual titanium oxide coating, the uppermost adsorbate layers and atom layers (10-20 nm) are removed beforehand by sputtering.

X-ray photoelectron spectroscopy (XPS; often also "electron spectroscopy for chemical analysis", ESCA) is an established method from the photoelectron spectroscopy (PES) group for the non-destructive determination of the chemical composition of solids, or the surface thereof. It initially delivers a qualitative elemental analysis, that is to say information regarding the chemical elements of which the solid, or the surface thereof, is composed. Only hydrogen and helium cannot directly be detected, on account of low effective cross-sections. The most common X-ray sources for use in XPS are Al—$K_\alpha$ or also Mg—$K_\alpha$ sources, wherein other X-ray sources, however, also generate silicon, titanium or zirconium X-ray lines. In addition to X-ray tubes, increasing use is also being made of synchrotron radiation which, on account of the virtually unlimited variability of the photon energy and monochromy, is suitable as the excitation source for the range of the accessible exciting photon energies from a few discrete values (e.g. Al—$K_\alpha$, hv=1486.6 eV and Mg—$K_\alpha$, hv=1253.6 eV) to a continuum of several electron volts to 20 keV.

However, because measurements by means of synchrotron radiation require a very high technical and thus financial outlay, the mentioned alternative X-ray sources are widely used in standard XPS analyses. The energy of the photoelectrons generated with those X-ray sources is in the range between 0 and 1500 eV, which means, for PES measurements, that the emitted electrons originate from a maximum depth of the studied sample situated between 0 and 100 Å. The limiting factor here is the mean free path of electrons in the solid. As a result, XPS is predominantly used for the analysis of solid surfaces. The analyzer used for the XPS measurement (e.g. a hemispherical analyzer) is so adjusted via electrostatic lenses and countervoltages that only electrons of a specific energy are able to pass. For the XPS measurement, the electrons that arrive at the end of the analyzer are detected by a secondary electron multiplier so that a spectrum forms, which is represented in a graph by plotting the intensity (count rate) over the kinetic energy of the photoelectrons. A quantitative evaluation of the spectral lines obtained by XPS measurements is carried out via the intensity thereof. The intensity, that is to say the count rate of these measurements, is proportional to the frequency of the occurrence of the various elements in the sample. In order to determine the chemical composition of a solid or of a surface, given, for example, as at. % (atomic %), the area under the observed lines which are characteristic of the elements is evaluated. The person skilled in the art is familiar with the measurement-specific particularities which are to be taken into account in order to ensure measurement accuracy and with corrective actions, such as, for example: background subtraction (in particular linear background correction, Shirley background correction or Tougaard background correction); correction of the values for the areas which are determined under the respective lines, by so-called sensitivity factors or effective cross-sections; or the loss rate dependent on the kinetic energy of the photoelectrons and the composition of the solid, an effect which can be accommodated by taking into consideration the mean free path of the electrons in the solid or in the surface. Corresponding correction data are available to the person skilled in the art at least for most elements and simple compounds in various tables.

The coating provided according to the invention is characterized in one feature by its chemical composition in that it comprises as the main constituents titanium and oxygen and always a small residual amount of carbon remaining from the coating process or, where halogen-containing precursors have been used in the coating process, a small optional residual amount of halide remaining from the coating process (but in that case no carbon), or consists of the mentioned elements. The main constituents of the coating, titanium and oxygen, can each be present individually in the ranges of amounts given below in at. %; molar ratios of titanium to oxygen of 0.727:2 to 1.19:2, preferably from 0.871:2 to 1.028:2, and particularly preferably of approximately 1:2 are expedient. That is to say, the main constituent of the coating is formed substantially of titanium dioxide.

The minor constituents from the coating process, such as carbon and/or halide, but preferably carbon, can be present in an amount of up to 15 at. %, based on the total number of all the atoms of the coating without H as 100 at. %. In the case of carbon-containing precursors, the amount of the minor constituent carbon is preferably in the range of from 0.05 to 15 at. %, preferably from 0.1 to 10 at. %, particularly preferably from 0.2 to 5 at. %, based on the total number of all the atoms of the coating without H as 100 at. %. In the case of halogen-containing precursors, the amount of the minor constituent halide is preferably in the range of from 0.01 to 10 at. %, preferably from 0.05 to 5 at. %, particularly preferably from 0.1 to 1 at. %, based on the total number of all the atoms of the coating without H as 100 at. %, all values being measured by means of XPS. In principle, when halide-containing precursors are used instead of C-containing precursors, the respective halide is detectable in the coating instead of C. The preferred halide is chlorine. In addition, the comments and preferred embodiments in this text apply analogously to the use of halide-containing precursors and to the layers produced therefrom.

In one embodiment of the invention, the invention relates to a medical implant or medical instrument, wherein the coating, measured by means of XPS, and based on the total number of all the atoms of the coating (as 100 at. %) without H (hydrogen), comprises or consists of O: from 55.0 at. % to 75 at. %
Ti: from 20 at. % to 44.5 at. %
C: from 0.05 to 15 at. %, preferably from 0.1 to 10 at. %, particularly preferably from 0.2 to 5 at. %, most particularly preferably from 0.5 at. % to 5 at. %.

The invention hereby relates preferably to a medical implant or medical instrument, wherein the coating, measured by means of XPS, and based on the total number of all the atoms of the coating (as 100 at. %) without H (hydrogen), comprises or consists of O: from 62.0 at. % to 72 at. %
Ti: from 27 at. % to 37 at. % and
C: from 0.1 to 10 at. %, preferably from 0.2 to 5 at. %, particularly preferably from 0.5 at. % to 5 at. %, most particularly preferably from 0.7 at. % to 3.5 at. %.

The possible proportion of carbon in the layers can be from 0.05 at. % to 15.0 at. % as an upper limit which is expedient in practice. A narrower expedient range for the proportion of carbon is, for example, from 0.1 to 10.0 at. %.

Within the context of the invention, the layers can in some cases also have a small proportion of nitrogen (N). It is not important whether this proportion of nitrogen was introduced into the layer during storage, during transport or during preparation of the substrate for XPS measurements (e.g. during removal of the uppermost 10-20 nm layer by sputtering). It is also not important whether the proportion of nitrogen was incorporated into the layer during the coating process, that is to say via the incorporation of carrier gas molecules, for example when using nitrogen as the carrier gas or inert gas. The proportion of nitrogen can be determined by XPS measurements. In XPS characterizations of coated substrates from the method according to the invention, a proportion of nitrogen of from 0 to 2.5 at. % may be found. In coated substrates produced according to the invention, a proportion of nitrogen of, for example, 2.1 at. %, 1.5 at. %, 0.8 at. % or 0.6 at. % has been determined. (In each case based on the total number of all the atoms of the coating without H, determined by means of XPS).

The layer thickness of the coating according to the invention is dependent on the desired color of the coating, the optical properties of the substrate, the particle content and the homogeneity of the coating. Preferred layers are particle-free. The preferred range of the layer thickness of the coating according to the invention is between 15 nm and about 370 nm. Accordingly, there is preferably provided according to the invention a medical implant or medical instrument wherein the colored marking in the form of a coating has a layer thickness of from 10 nm to 600 nm, preferably from 15 nm to 370 nm. In a typical but non-limiting example, the layer thickness is approximately from 110 nm to 127 nm for a pink- to violet-colored coating.

The optical properties of the coating according to the invention, such as refractive index and reflectivity, are dependent on the coating parameters, the particle content and the homogeneity of the coating (increase in color brilliance by reducing parasitic particle formation). They can further be influenced by thermal after-treatment of the coating or by the substrate temperature during the coating. The optical properties can thus be adjusted according to the requirements made in an individual case. The markedness of the interference color can further be influenced by the layer thickness, the substrate material and the pretreatment of the surface.

The chromaticity of the coating according to the invention is thus dependent on the layer thickness, the optical properties of the coating material and of the substrate material, and can thus likewise be adjusted according to the requirements made in a particular case, for example to the following possible colors: brown, yellow, golden yellow, pink, rose pink, violet, purple, blue, dark blue, light blue, turquoise, greenish blue, greenish yellow, green, light green, dark green. An invisible coloration (colorless) is also possible. A typical example, without implying any limitation, has a pink to violet coloration on polished steel products.

The coatings according to the invention surprisingly exhibit excellent adhesion to the substrates mentioned in the following, which adhesion can be adjusted and/or optimized in particular in dependence on the coating parameters, the layer thickness produced, the pretreatment of the substrate surface, the thermal after-treatment of the coating. The adhesion is empirical, and the determination of a typical adhesion requires the test method used to be indicated. In the simplest case, whether and to what extent the coating delaminates partially or completely from the substrate as a result of treatment in the adhesion test is assessed visually or optionally also using a microscope.

The adhesion of the coating according to the invention to the substrate can be tested, for example, by a so-called peel test or by a so-called Steri-Test. In the peel test, adequate adhesion of the coating is simply tested using an adhesive tape, which is first pressed onto the coating, optionally with application of a specified pressure and/or for a specified period of time, and then, optionally after a specified waiting time, is peeled off the substrate again. It is then checked, in the simplest case, for example, visually and optionally also using a microscope, whether and to what extent the coating delaminates partially or completely upon removal of the adhesive tape, that is to say is partially or completely detached from the substrate with the adhesive tape. The test can be repeated in cycles.

In the so-called Steri-Test, adequate adhesion of the coating is tested by first cleaning the coating on the substrate with an alkaline cleaning agent and then carrying out an after-treatment in a steam autoclave (therefore "Steri-Test"). It is thereby checked whether the coating delaminates during the test, that is to say whether it flakes from the surface of the substrate under the high pressures in the autoclave or during vacuum drying, which can be recognized by a change in the color of the layer. Where the coating is detached only very slightly, at least a discernible local color change indicates delamination. A visual assessment of the coating after the Steri-Test thus permits reliable detection of any delamination, or of adhesion. The Steri-Test can also be repeated in cycles. In the case of the preferred coatings according to the invention, a loss of adhesion is not detectable, for example, even after 10 test cycles. Therefore, there is preferably provided a medical implant or medical instrument wherein the colored marking in the form of a coating has sufficient adhesion that no detachment and thus no color change occurs in 10 Steri-Test cycles. The performance of the Steri-Test is described in Example 3 (below).

Preference is given according to the invention to a medical implant or medical instrument wherein the colored marking in the form of a coating is a CVD layer. There is thus provided according to the invention a substrate having a colored marking in the form of a medical implant or medical instrument having a titanium dioxide layer, wherein into the titanium dioxide layer has been deposited by means of a CVD process, preferably by means of an atmospheric CVD process.

Materials which can be used for the substrate within the context of the invention are very varied and extend, for example, without limiting the suitable substrates, to materials having reflective surfaces. A typical example is electropolished stainless steel, in particular, for example, medical stainless steel of type DIN 1.4441 (implant grade). The nature of the substrates which can be used within the context of the invention preferably extends to the group of medical technology products, in particular medical instruments and also medical implants (e.g. in the form of screws, bone nails, plates, etc.).

Depending on the type, form and/or purpose of the medical implant or medical instrument, the coating can be applied to the entire surface or to a portion of the surface, in particular only to a particular portion (or region) or optionally a plurality of particular portions (or regions) of the surface. The local delimitation of the layer is hereby dependent on the local application of the coating materials, the flow dynamics in the region surrounding the area to be coated or the use of masking of portions of the substrate surface. A preferred variant relates to the use of a mask in order, for example in the case of implant screws, to produce a coating only on the screw head.

Accordingly, there is provided according to the invention preferably a medical implant or medical instrument wherein the colored marking in the form of a coating is applied only to a portion of the surface of the implant. A typical, non-limiting example is, therefore, the local coating of implant screws (coating on the screw head).

The medical implant or medical instrument according to the invention can comprise or consist of many different materials which are conventional for that purpose in the prior art and where possible are biocompatible, if desired permanent and/or also bioresorbable.

Accordingly, there is provided in one embodiment of the invention a medical implant or medical instrument wherein the material of the implant or of the instrument, preferably the material of the implant, to which the colored marking in the form of a coating is applied is selected from the group consisting of steel, stainless steel, titanium, magnesium, titanium and/or magnesium alloys, for example also with aluminum, cobalt-chromium alloys, polymeric material, in particular PEEK (polyether ether ketone), in particular also in composite structures, ceramics material, in particular aluminum oxide and/or zirconium oxide, fiber composites. Important materials are in particular stainless steel and titanium, and optionally also alloys with titanium.

If titanium is used, it can be present as pure titanium (in particular material no. 3.7025 or 3.7035) or titanium alloys. Examples of such titanium alloys are: Ti-6A1-4V, Ti-6A1-7Nb, Ti-5A1-2.5Fe, Ti-13Nb-13Zr and Ti-12Mo-6Zr-2Fe. If magnesium is used, it can be present as pure magnesium or magnesium alloys. An example of such magnesium alloys is AZ91.

Within the context of the invention, any medical implant or medical instrument that is conventional in practice by its type, nature, form and/or purpose can be provided on its surface or on one or more portions of its surface with at least one colored marking according to the invention in the form of a coating comprising or consisting of Ti (titanium) and O (oxygen) and C (carbon) and optionally halide. The amounts indicated above of the individual elements in the coating preferably apply. In some cases, it can be preferred that the implant surface in the region of the marking is not black.

In a preferred embodiment of the invention there is provided a medical implant wherein the implant is selected from the group consisting of screw, bone nail, plate. There are further suitable as the medical implant preferably also osteosynthesis plates, so-called spinal rods, and Kirschner wire.

The invention relates also to the use of a coating as defined above for the colored marking of a medical implant or medical instrument, preferably for the colored marking of a medical implant. All the comments made above in relation to the medical products according to the invention and the method according to the invention apply analogously to the use according to the invention.

The method used according to the invention is particularly important for achieving the object underlying the invention. The object is preferably achieved by means of the method according to the invention in that metal organic or organometallic titanium precursors are finely atomized and/or vaporized at atmospheric pressure by a heated, inert carrier gas and hydrolyzed by means of the atmospheric moisture in the environment of an application system. The reaction products formed thereby are deposited on the surface of medical technology materials and form titanium oxide layers which, however, have a proportion of carbon, which can be varied via the process parameters. The interference color appearance of the coating is dependent primarily on the deposited layer thickness and can purposively be adjusted by the degree of moisture in the environment of the coating nozzle, the chemistry of the starting material used for the coating, the distance between the coating nozzle and the sample, the process speed, the geometry of the coating nozzle, the change in the corresponding flows and the mixtures thereof. By adapting the coating parameters, the reactivity of the titanium precursor can be influenced to such an extent that both homogeneous, clear coatings as well as structured layer systems having a defined content of $TiO_2$ particle inclusions can be produced. The adhesion of the layers to the substrate materials, such as, for example, steel, can be improved by suitable pretreatment of the substrate, for example atmospheric-pressure plasma treatment, and/or an elevated substrate temperature or tempering of the substrate during application of the coating and/or tempering after application of the coating. As a result of a variation in the refractive index or the layer thickness of the coating, the thermal after-treatment of the substrate can lead to a change in the observed interference color. The invention hereby exhibits a technological strength which is superior to that of previous methods of the prior art. Compared to products with titanium oxide layers on medical technology materials which have been produced by methods of the prior art, the invention offers, as compared with those methods, significant cost benefits, significant performance advantages and as good as no barriers to introduction onto the market.

Accordingly, the invention relates also to a method for producing a medical implant according to the invention or a medical instrument according to the invention, comprising the steps:

a) providing a medical implant or a medical instrument as the substrate, b) providing a Ti-containing metal organic and/or organometallic precursor, c) optionally cleaning, structuring, smoothing and/or activating the substrate, d) depositing the precursor onto the substrate surface in the presence of water vapor, so that a layer formation takes place, e) optionally subjecting the coating on the product to after-treatment, wherein the after-treatment takes place thermally, by means of a laser and/or by means of plasma.

Pretreatment by means of a laser can also take place before step d).

It is preferred that the substrate is heated during step c) to not more than 250° C., more preferably to not more than 200° C., yet more preferably to not more than 150° C. and most particularly preferably not at all.

In particular, the invention relates also to a method for producing a medical implant according to the invention or a medical instrument according to the invention, comprising the steps:

a) providing a medical implant or a medical instrument, b) providing a Ti-containing metal organic or organometallic precursor, c) optionally cleaning, structuring, smoothing and/or activating the substrate (i.e. the surface of the medical implant or of the medical instrument), d) depositing the precursor on the substrate surface (i.e. on the surface of the medical implant or of the medical instrument) in the presence of water vapor, so that the formation of a coating comprising or consisting of Ti (titanium) and O (oxygen) and C (carbon) takes place; preferably the formation of a coating comprising or consisting of ≥85 at. %, preferably ≥90 at. %, particularly preferably ≥95 at. % and most particularly preferably ≥98 at. %, in each case based on the total number of all the atoms of the coating (as 100 at. %) without H (hydrogen), Ti (titanium) and O (oxygen) and C (carbon);

e) optionally subjecting the coating on the product to after-treatment, wherein the after-treatment takes place thermally, by means of a laser and/or by means of plasma.

In one embodiment, the invention relates to an above process wherein step d) takes place under atmospheric influence and/or with an additional infeed of water, preferably in vapor form. In expedient embodiments of this method of the invention, the water vapor is fed in in a ratio by volume of the liquids of precursor to be vaporized to water of from 9:1 to 1:100, preferably from 9:1 to 1:20.

In a preferred embodiment of the method according to the invention, the precursor is selected from the group of the titanium alkoxides, titanium organyls, titanium phenolates; preferably from the group of the titanium alkoxides.

Preferred titanium compounds (precursors) from the group of the titanium alkoxides, all of which can be used in principle, are titanium propoxide and titanium butoxide, in particular titanium isopropoxide (TTIP).

In addition to Ti-containing metal organic or organometallic precursors, titanium halides can also be used as precursors. Titanium chloride is especially suitable. In this case, the Ti, O and C composition of the coating will possibly change slightly as a result of a proportion of a halide, since the layers may then also contain a certain proportion of halogen; titanium halides can also be used in addition to Ti precursors that yield carbon. Carbon does not occur in layers produced solely from titanium halide precursors.

Accordingly, there is also possible a medical implant or medical instrument which comprises on its surface a colored marking in the form of a coating, wherein the coating comprises Ti, O and C and/or halides, measured by means of XPS, in an amount of ≥85 at. %, preferably ≥90 at. %, particularly preferably ≥95 at. % and most particularly preferably ≥98 at. %, in each case based on the total number of all the atoms of the coating without H, and a corresponding production method. It should be noted that the preferred embodiments also apply analogously to the use of halide-containing precursors, where the halide contents mentioned in the text (where only halide-containing inorganic titanium precursors are used) occur instead of the carbon content, or the corresponding halide content is added to the carbon content, where both organic and halide-containing titanium precursors are used for the layer deposition.

Further possible titanium precursors are titanic acid esters, a supergroup which also includes the titanium alkoxides, and mention is to be made of the titanium phenolates as a further subgroup. Titanic acid esters have the general form $Ti(OR)_4$ or $TiHal_2(OR)_2$ (Hal=halogen, R=alkyl radical). A halogen-containing example is $TiCl_2(OEt)_2$. In the case of these halogen-containing compounds too, a certain proportion of halogens could result in the layer. An example of a titanium phenolate is titanium tetraphenoxide.

Further possible titanium precursors are additionally titanium organyls of the type of the titanium alkyl compounds $TiR_4$ (R=alkyl radical). An example is tetraphenyl titanium; these compounds have only limited stability, however.

In addition to precursors which yield carbon, titanium salts may optionally also be used as precursors: for example, titanium sulfate or titanium oxide sulfate (titanyl sulfate). As with the halides, the layers should in this case too exhibit a slightly different composition and, for example, comprise a small proportion of sulfur.

In a preferred embodiment of the method according to the invention, the precursor is deposited using at least one nozzle and/or one or more carrier gases.

The coating process will be explained in greater detail in the following, in particular with reference to process parameters.

The coating process for the colored marking of medical products can preferably take place, depending on the geometry of the material to be coated and the properties of the layer to be produced, either directly in the atmosphere or in a chamber system which is open to the atmosphere. The chamber system can thereby be used to reduce the residual moisture in the atmosphere surrounding the product to be coated, by means of a dry gas stream, in order thus better to be able to control the coating process.

The first step of the coating process is pretreatment of the product surface by means of a thermal, mechanical, laser and/or plasma method. This step serves both to clean and activate the surface before the actual coating. This step too can be carried out in a chamber system which is open to the atmosphere with defined atmospheric moisture.

The actual coating process takes place as the hydrolysis of a suitable titanium-containing precursor. The precursor is vaporized or atomized in a defined amount in a heated carrier gas stream and applied to the surface of the product to be coated by means of a directed gas flow from a nozzle. Depending on the application, it may also be expedient additionally to heat the nozzle itself again in order to prevent the precursor from recondensing. The reaction partner can be, on the one hand, the atmospheric moisture present in the surrounding gas atmosphere. On the other hand, a defined amount of moisture can be introduced into the atmosphere surrounding the product to be coated by means of a second nozzle system, in order to influence the reactivity of the precursor and thus the rate of layer formation on the surface. The application of the moisture also takes place by means of a directed gas flow in a heated or unheated carrier gas stream. In order to influence the optical properties and the homogeneity of the layer, the infeed parameters of the coating nozzle and the moisture nozzle can be chosen accordingly. The homogeneity of the coating can additionally also be influenced by rotating the product to be coated. It is further possible to use a coaxial nozzle which combines the coating nozzle and the moisture nozzle and thus influences the properties and the homogeneity of the titanium oxide layers. A further influencing factor is the temperature of the sample during the coating. Heating of the sample can thereby take place directly during the coating process or can be carried out within the context of a pretreatment. Heating only during the pretreatment leads to a falling substrate temperature during the coating process, whereby a further possibility for varying the layer properties can be achieved. The coated product can be heated again after the actual coating process, whereby the refractive index of the layer, the layer adhesion, the layer crosslinking and the carbon content of the layer can be influenced. In addition, the adhesion of the coating to the substrate can optionally be increased by the additional post-tempering.

The distance of the precursor coating nozzle from the substrate is governed by the dimensions of the coating nozzle, the carrier gas flow used, the geometry of the substrate to be coated, the infeed angle of the coating nozzle in relation to the substrate normal, the dimensions of the moisture nozzle, the carrier gas flow in the moisture nozzle, the infeed angle of the moisture nozzle in relation to the substrate normal, the distance of the moisture nozzle from the substrate, the desired rate of layer formation on the substrate surface, and the particle content of the coating to be produced. A preferred range for the distance of the precursor coating nozzle from the substrate is from 5 mm to 100 mm. In a typical but non-limiting example, the distance is 20 mm for producing a low-powder titanium oxide coating in particular on a steel screw.

The infeed angle of the precursor coating nozzle in relation to the substrate normal is governed by the dimensions of the coating nozzle, the carrier gas flow used, the geometry of the substrate to be coated, the distance of the coating nozzle from the substrate, the dimensions of the coating nozzle, the carrier gas flow in the moisture nozzle, the infeed angle of the moisture nozzle in relation to the substrate normal, the distance of the moisture nozzle from the substrate, the desired rate of layer formation on the substrate surface, and the particle content of the coating to be produced. A typical range, without implying any limitation, is between 0° (parallel to the substrate or sample normal) and 180° (metering from beneath the sample or substrate). In a typical parameter example the infeed angle, without implying any limitation, is 45° for producing a low-powder titanium oxide coating on a steel screw.

The dimensions and shape of the coating nozzle are governed by the carrier gas flow used, the amount of precursor used, the geometry of the substrate to be coated, the distance of the coating nozzle from the substrate, the infeed angle of the coating nozzle in relation to the substrate or sample normal, the dimensions of the moisture nozzle, the carrier gas flow in the moisture nozzle, the infeed angle of the moisture nozzle in relation to the substrate normal, the distance of the moisture nozzle from the substrate, the desired rate of layer formation on the substrate surface, and the particle content of the coating to be produced. The following shapes are preferred: tubular, elliptical, square, rectangular, slit-like nozzles, etc. It is also possible to use a plurality of single nozzles. In a typical but non-limiting example, a tubular nozzle having an inside tube diameter of 4.0 mm is used for producing a low-powder titanium oxide coating on a steel screw.

The type of precursors used is governed by the reaction mechanism and the reactivity of the precursor towards water. The above-mentioned precursors can be used, individually or in combination with one another, but according to the invention at least one precursor must always be a carbon-containing and/or halogen-containing precursor. Titanium alkoxides are found to be the class of compounds that is advantageously to be used. An example of a typical titanium alkoxide compound, without implying any limitation, is titanium isopropoxide (TTIP; CAS number: 546-68-9; alternative names: titanium tetraisopropoxide, tetraisopropyl orthotitanate and tetraisopropyl titanate).

The amount of precursors used is governed by the carrier gas flow used, the geometry of the coating nozzle, the desired rate of layer formation on the substrate surface, and the particle content of the coating to be produced. A preferred range of amounts of the precursors used is from 0.5 µl/min to 50 µl/min. A typical but non-limiting parameter example uses 9 µl/min for producing a low-powder titanium oxide coating on a steel screw.

The distance of the optional moisture nozzle from the substrate is governed by the dimensions of the moisture nozzle, the carrier gas flow used, the geometry of the substrate to be coated, the infeed angle of the moisture nozzle in relation to the substrate normal, the dimensions of the coating nozzle, the carrier gas flow in the coating nozzle, the infeed angle of the coating nozzle in relation to the sample normal, the distance of the coating nozzle from the substrate, the desired rate of layer formation on the substrate surface, and the particle content of the coating to be produced. A preferred range for the distance of the moisture nozzle from the substrate is from 5 mm to 100 mm. In a typical but non-limiting example, the distance is 20 mm for producing a low-powder titanium oxide coating in particular on a steel screw.

The infeed angle of the moisture nozzle in relation to the substrate normal is governed by the dimensions of the moisture nozzle, the carrier gas flow used, the geometry of the substrate to be coated, the distance of the moisture nozzle from the substrate, the dimensions of the coating nozzle, the carrier gas flow in the coating nozzle, the infeed angle of the coating nozzle in relation to the sample normal, the distance of the coating nozzle from the substrate, the desired rate of layer formation on the substrate surface, and the particle content of the coating to be produced. A typical range, without implying any limitation, is between 0° (parallel to the substrate or sample normal) and 180° (metering from beneath the sample or substrate). In a typical but non-limiting example, the infeed angle is 45° for producing a low-powder titanium oxide coating on a steel screw.

The dimensions and shape of the moisture nozzle are governed by the carrier gas flow used, the amount of moisture used, the geometry of the substrate to be coated, the distance of the moisture nozzle from the substrate, the infeed angle of the moisture nozzle in relation to the sample normal, the dimensions of the coating nozzle, the carrier gas flow in the coating nozzle, the infeed angle of the coating nozzle in relation to the sample normal, the distance of the coating nozzle from the substrate, the desired rate of layer formation on the substrate surface, and the particle content of the coating to be produced. The following shapes are possible: tubular, elliptical, square, rectangular, slit-like nozzles, etc. It is also possible to use a plurality of single nozzles. In a typical example, without implying any limitation, a tubular nozzle having an inside tube diameter of 4.0 mm is used for producing a low-powder titanium oxide coating on a steel screw.

Within the context of the invention, it is also possible and optionally preferred to use a coaxial nozzle with a combined precursor and moisture infeed. The use of a coaxial nozzle with a combined precursor and moisture infeed is governed in principle by the same parameters as for a single coating nozzle, for example as described above. Additional further parameters are the distance and the relative position between the nozzle end of the precursor infeed and the moisture infeed. The expedient distance of the coaxial nozzle corresponds in principle to that for a single coating nozzle, for example as described above. The distance between the nozzle part of the precursor infeed and the moisture infeed can be in the range from +50 mm (nozzle end for the precursor infeed closer to the substrate surface) to −50 mm (nozzle end for the moisture infeed closer to the substrate surface). A typical but non-limiting example of a coaxial nozzle is two tubular nozzles fitted inside one another, with an inside tube diameter of 0.51 mm for the coating nozzle and 4.0 mm for the moisture nozzle; the nozzle ends are at the same height, that is to say the distance is 0 mm.

The amount of moisture used in the method according to the invention is governed by the carrier gas flow that is established, the temperature of the carrier gas (which influences the saturation quantity of water vapor), the desired rate of layer formation on the substrate surface, the amount of precursor used, the carrier gas flow in the coating nozzle, and the particle content of the coating to be produced. A typical preferred range for the amount of moisture is from 0.01 ml of water to be vaporized per $m^3$ of carrier gas to 590.0 ml of water to be vaporized per $m^3$ of carrier gas. In a typical example, the amount of moisture, without implying any limitation, is approximately 18.2 ml of water to be vaporized per $m^3$ of carrier gas for a moisture infeed with a carrier gas flow rate of 2.35 l/min with a precursor infeed with an amount of precursor of 9 µl/min and a carrier gas flow rate for the precursor of 5.0 l/min.

The choice of the carrier gas to be used for the precursor infeed is governed by the reactivity towards the precursor and the residual moisture content. Carrier gases which can be used according to the invention are, for example, dry compressed air or dry nitrogen. In expedient examples, nitrogen of purity class 5.0 is used.

The amount of carrier gas used for the precursor infeed is governed by the amount of precursor used, the dimensions and shape of the coating nozzle, the distance of the coating nozzle from the substrate, the infeed angle of the coating nozzle in relation to the substrate normal, the carrier gas flow in the moisture nozzle, the geometry of the substrate to be coated, the desired rate of layer formation on the substrate surface, and the particle content of the coating to be produced. A preferred range for the amount of carrier gas is from 0.5 l/min to 15 l/min. In a typical but non-limiting example, the amount of carrier gas is 5 l/min of nitrogen for producing a low-powder titanium oxide coating on a steel screw.

The amount of carrier gas used for the optional moisture nozzle is governed by the amount of moisture to be fed in (amount of water to be fed in), the temperature of the carrier gas (which influences the saturation quantity of water vapor), the dimensions and shape of the moisture nozzle, the distance of the moisture nozzle from the substrate, the infeed angle of the moisture nozzle in relation to the substrate normal, the carrier gas flow in the coating nozzle, the geometry of the substrate to be coated, the desired rate of layer formation on the substrate surface, and the particle content of the coating to be produced. A preferred range for the amount of carrier gas is from 0.05 l/min to 10 l/min. In a typical but non-limiting example, the amount of carrier gas is 2.35 l/min of nitrogen for producing a low-powder titanium oxide coating on a steel screw.

The vaporizer temperature for the precursor infeed is governed by the precursor compound used, the carrier gas flow used, the amount of precursor used, the shape and dimensions of the coating nozzle. For example, the vaporizer temperature can be approximately 160° C.

The vaporizer temperature for the moisture infeed is governed by the amount of moisture used, the saturation quantity of water vapor in the carrier gas used at the particular temperature, the carrier gas flow used. The vaporizer temperature, without the use of heating, can be at room temperature, for example approximately 22° C. In a further example, the vaporizer temperature is approximately 150° C. through the use of heating.

Additional heating can optionally be used for the coating nozzle. The temperature of an optional additional heating for the coating nozzle is then governed by the precursor compound used, the carrier gas flow used, the amount of precursor used, the shape and dimensions of the coating nozzle. For example, the heating temperature of the coating nozzle can be a temperature of 80° C. In a further example, the heating temperature of the coating nozzle is approximately 150° C.

The relative proportion of precursor to water (moisture) is governed by the geometry of the substrate to be coated, the shape and dimensions of the coating nozzle, the carrier gas flow in the coating nozzle, the distance of the coating nozzle from the substrate, the infeed angle of the coating nozzle in relation to the substrate normal, the shape and dimensions of the moisture nozzle, the carrier gas flow in the moisture nozzle, the distance of the moisture nozzle from the substrate, the infeed angle of the moisture nozzle in relation to the substrate normal, the desired rate of layer formation on the substrate surface, and the particle content of the coating to be produced. A preferred range for the relative proportion of precursor to water (moisture), expressed as the amount of precursor (µl/min) to the amount of water (µl/min), is from 9:1 to 1:100. For example, an expedient relative proportion of precursor (µl/min) to water (µl/min) can be 1:4.76.

Various types of pretreatment are suitable for pretreating or activating the substrate before the coating, such as, for example, wet-chemical pretreatment, thermal pretreatment, laser pretreatment, plasma pretreatment (especially with atmospheric-pressure plasmas); if desired, the pretreatment or activation can also be carried out under an inert gas atmosphere; combinations are also possible. The pretreatment method can thus also be a wet-chemical treatment optionally using ultrasound and/or elevated temperatures. In the case of plasma pretreatment, there can be used, for example, low-pressure plasma treatment and atmospheric-pressure plasma treatment, in each case with different types of plasma sources and/or ionization gases. There are suitable for thermal pretreatment, for example, infrared heating, inductive heating and resistance heating. A typical example of an expedient pretreatment or activation of the substrate, without implying any limitation, is atmospheric-pressure plasma pretreatment with a plasma jet source using dry compressed air as the ionization gas.

The substrate temperature during the coating is governed by the refractive index of the coating to be produced, the desired rate of layer formation on the substrate surface, the particle content and the crystallinity of the coating to be produced. The temperature of the substrate can also change during the coating. A typical but non-limiting example of a falling substrate temperature during the coating is a substrate temperature which starts at approximately 180° C. and falls to lower temperatures.

The nature of the substrate heating during the coating can take place by various heating methods, for example by infrared heating, inductive heating, resistance heating, heating by the heated carrier gas. Heating can also take place within the context of a pretreatment, wherein the substrate then cools down during the coating, that is to say a falling substrate temperature is present during the coating. A typical but non-limiting example is heating of the substrate at 180° C. during pretreatment with an atmospheric-pressure plasma jet source; during the coating, the substrate cools down in the heated carrier gas stream; alternatively, the pretreatment can also be carried out with induction heating.

The sample or substrate can optionally be rotated during the coating. The rotation of the sample or substrate, including the speed of rotation, is then governed by the geometry and the dimensions of the product to be coated, the desired homogeneity of the coating. A typical example of the rotation of a sample or substrate, without implying any limitation, operates at a speed of rotation of 175 rpm for the coating of a screw head of a medical implant screw made of steel.

According to the invention, post-tempering of the samples or substrates can optionally be provided after coating has taken place. The nature of the sample or substrate heating for the post-tempering of the substrate after coating has taken place can take place by one of the above-mentioned heating methods, for example by infrared heating, inductive heating, resistance heating, and also by circulating air heating (circulating air oven). The temperature used for the optional post-tempering of the samples or substrates after coating has taken place is governed by the heating method used for the post-tempering, the heating time used for the post-tempering, the chemical composition of the coating, the desired refractive index of the coating to be produced, the desired particle content and the desired crystallinity of the coating to be produced. A preferred range for the temperature of the optional post-tempering is from 0° C. to 450° C., whereby the formation of anatase can occur in the region of the upper limit of the temperature. The heating time for the optional post-tempering of the samples or substrates after coating has taken place is governed by the heating method used for the post-tempering, the heating temperature used for the post-tempering, the chemical composition of the coating, the desired refractive index of the coating to be produced, the desired particle content and the desired crystallinity of the coating to be produced. A typical example of a post-tempering, without implying any limitation, is heating of the sample or substrate at 150° C. for 30 min. in a circulating air oven in order to improve the adhesion of the coating. The after-treatment can also take place by means of plasma or a laser, an example of a suitable laser is: Nd:YAG laser with a wavelength of 1064 nm.

The chosen titanium-containing, metal organic, organometallic or inorganic compounds, in particular titanium tetraisopropoxide (TTIP), have high reactivity towards water, with the formation of titanium oxide reaction products. The application of a defined amount of the starting compound in the form of a finely divided vapor allows, with suitably chosen process parameters, titanium oxide layer systems to be deposited on surfaces. An additional excitation source, such as, for example, temperature, is not necessary for this process.

The layers produced in this manner have a chemical composition which corresponds approximately to titanium dioxide with an addition of carbon.

The coatings influence the reflection of white light in that a superposition of the rays reflected at the surface of the layer, or the lower boundary surface, at specific wavelengths leads to a destructive interference. Since the remaining wavelengths are retained, the reflected light frequently appears colored. The interference colors of the surface that are thereby produced are influenced by the substrate properties and the thickness of the titanium oxide coating and can accordingly be adjusted.

Application to medical technology products yields a biocompatible, colored marking of the materials, in order to make them visually better distinguishable and perceivable. Examples thereof are special implant screws for specific applications, which are marked by means of the coating technique according to the invention with a magenta-colored titanium oxide layer on the screw head so that they can easily be distinguished visually from implant screws of a comparable structure.

The use of the coating techniques of the prior art, such as, for example, physical vapor deposition (PVD) or sputter deposition, is associated with a significantly greater technical, financial and time-related outlay compared with the method according to the invention and produces coatings with different morphologies, the adhesion of which can sometimes be inadequate. The coatings according to the invention can be detected by microscopic analysis of the morphology or spectroscopic analyses of the layers, even in the region close to the boundary with the substrate surface, and distinguished from the coatings of the prior art. Since the deposition mechanism according to the invention is based on a hydrolysis reaction, the coatings according to the invention that are produced have a characteristic chemical composition and structure. Any $TiO_2$ particle inclusions present can also give information regarding nature of the coating and be used to distinguish it.

The coatings or coating systems according to the invention are suitable for many different fields of application. Special mention may be made here of medical technology products, in particular implants (e.g. screws, bone nails, plates, and, for example, other implants mentioned above), which have been provided with titanium oxide coatings according to the invention in order to permit visual allocation of the products.

The method according to the invention for producing the coating according to the invention on medical technology products can take the form of a large-scale method, for example as an in-line- and single piece flow-capable method for producing biocompatible colored markings and/or for marking medical technology products having different geometries.

The invention will be explained in greater detail by means of the following examples, without limiting the scope thereof.

EXAMPLE 1: CHEMICAL COMPOSITION OF COATINGS

Chemical composition of a coating according to the invention for coatings on thin flat substrates of polished silicon wafers (orientation 100); values for Ti, O, C from the XPS overlay spectra according to the following measurement parameters:

Excitation source: monochromatized $Al_{K\alpha}$ radiation

Analyzer setting: Constant Analyzer Energy mode (CAE) with 70 eV pass energy

Analysis area: 0.65 mm diameter

Sample neutralization: by means of low-energy electrons (4 eV).

In order to be able to determine the chemical composition of the actual titanium oxide coating, the uppermost 20 nm (adsorbate layers and uppermost atom layers) were removed before the XPS measurements by means of sputtering according to the following parameters:

Sputtering gas: argon

Acceleration voltage: 3 kV

Sputtering current: 1.6 µA

Sputtering time: 210 s.

The layer thicknesses of the titanium oxide coatings were determined by comparing the interference colors with a theoretical model for the colorimetric prediction of interference colors, which gives a direct relationship between the applied layer thickness and the resulting interference color. The principles of this theoretical model are comprehensively described in various literature sources, for example P. Wienhold and U. Littmark, E-MRS Symp. Proc., 1987, Vol. XVII, p. 441 ff or P. H. Berning, in Physics of Thin Films, Ed. G. Hass, Vol. 1, p. 69-121, Acad. Press 1963, New York or M. Born and E. Wolf, Principles of Optics, $6^{th}$ edn. Pergamon Press 1980, Oxford. A pure titanium oxide layer on an Si substrate was used as the basis for the theoretical calculations. The light source used was a standard D65 spectrum (which corresponds to normal daylight with an intensity maximum at a wavelength of about 460 nm).

The XPS measurements of the titanium dioxide coating gave the following results:
main constituents: titanium and oxygen in a ratio of approximately 1:2 (exactly: 0.82:2 or 0.84:2);
low carbon content from the coating process (residual content owing to the carbon-containing precursor).

| Composition 1 | Composition 2 |
|---|---|
| 130 nm layer thickness | 155 nm layer thickness |
| Oxygen: 67.9 at. % | Oxygen: 67.5 at. %; |
| Titanium: 27.9 at. % | Titanium: 28.3 at. %; |
| Carbon: 3.5 at. % | Carbon: 3.6 at. %. |

EXAMPLE 2: EXAMPLES OF COATING METHODS

Coating methods 1 and 2 were used to produce the samples from Example 1 ("Chemical composition of coatings"). The layer composition of these layers corresponds to composition 1 (coating method 1) or 2 (coating method 2) mentioned therein.

Coating methods 3 and 4 represent layer depositions on polished, medical stainless steel substrates (DIN 1.4441).

Coating Method 1:
substrate geometry: thin flat substrate (wafer);
coating setup: enclosed coating system with two separate infeeds for the titanium-containing precursor and the moisture;
titanium precursor: titanium isopropoxide;
carrier gas titanium precursor: nitrogen 5.0, 5 l/min;
amount of titanium precursor: 10 µl/min;
carrier gas moisture: nitrogen 5.0, 2 l/min;
ratio TTIP/water (amounts of liquid fed in): approximately 10 µl/min:55 µl/min=1:5.5;
angle moisture nozzle: 45°;
angle coating nozzle: 45°;
distance coating nozzle: approximately 29 mm;
distance moisture nozzle: approximately 29 mm;
sample mount: rotating, 175 rpm;
example of the color shade of the coating: violet, slightly yellowish in the edge region;
(coating time: about 80 s)
pretreatment: atmospheric-pressure plasma pretreatment with nitrogen as process gas, sample pre-tempering by the plasma at about 180° C.;
no post-tempering.

Coating Method 2:
substrate geometry: thin flat substrate (wafer);
coating setup: enclosed coating system with two separate infeeds for the titanium-containing precursor and the moisture;
titanium precursor: titanium isopropoxide;
carrier gas titanium precursor: nitrogen 5.0, 5 l/min;
amount of titanium precursor: 10 µl/min;
carrier gas moisture: nitrogen 5.0, 2 l/min;
ratio TTIP/water (amount of liquid fed in): approximately 10 µl/min:55 µl/min=1:5.5;
angle moisture nozzle: 45°;
angle coating nozzle: 45°;
distance coating nozzle: approximately 29 mm;
distance moisture nozzle: approximately 29 mm;
sample mount: rotating, 175 rpm;
example of color shade of the coating: greenish blue, tendency to violet in the center;
(coating time: about 90 s)
pretreatment: atmospheric-pressure plasma pretreatment with nitrogen as process gas, sample pre-tempering by the plasma to about 180° C.;
no post-tempering.

Coating Method 3:
substrate geometry: screw head (local coating of a screw);
coating setup: enclosed coating system with two separate infeeds for the titanium-containing precursor and the moisture;
titanium precursor: titanium isopropoxide
carrier gas titanium precursor: nitrogen 5.0, 5 l/min;
amount of titanium precursor: 9 µl/min;
carrier gas moisture: nitrogen 5.0, 2.35 l/min;
ratio TTIP/water (amount of liquid fed in): approximately 9 µl/min: 42.8 µl/min=1:4.76;
angle moisture nozzle: 45°;
angle coating nozzle: 45°;
distance coating nozzle: 20 mm;
distance moisture nozzle: 20 mm;
sample mount: rotating, 175 rpm, with mask for the screw;
example of color shade for the coating: rose pink to violet (coating time about 45 s)
pretreatment: induction heating, sample pre-tempering at 180° C.;
no post-tempering.

Coating Method 4:
substrate geometry: thicker flat substrate (coin) with a diameter of 25 mm
coating setup: treatment under atmospheric conditions without enclosed system;
only an infeed for the titanium-containing precursor was used; the residual moisture in the atmosphere served as the reaction partner;
titanium precursor: titanium isopropoxide;
carrier gas titanium precursor: nitrogen 5.0, 5 l/min;
amount of titanium precursor: 22 µl/min;
sample mount: mask, no rotation;
pretreatment: atmospheric-pressure plasma pretreatment with compressed air as the process gas;
example of the color shade of the coating: rose pink to violet coating, golden yellow in the edge region (coating time: about 2 s/cm²);
sample temperature during the coating: 80° C.
type of sample heating during coating: heating by heated substrate (resistance heating); —distance coating nozzle: 10 mm;
angle coating nozzle: 0° (perpendicular to the sample);
post-tempering: 150° C. for 30 min in a circulating air oven.

EXAMPLE 3: STERI-TEST FOR DETERMINING THE ADHESION

Testing the adhesion (Steri-Test) of coatings makes use of the following properties of the coatings: if the layers delaminate during the test, they flake from the surface immediately under the high pressures in the autoclave or during vacuum drying, which can be detected by the recurring substrate coloration. In the slightest case, a local color change is seen, which indicates delamination. A visual assessment is thus generally sufficient in this test.

Procedure for a Steri-Test Cycle

1. Alkaline cleaning (Deconex 28 Alka One from Borer Chemie (about pH 11)): preliminary cleaning (2 min), cleaning (10 min, 70° C.), neutralization with cold water (2 min), rinsing (2 min), thermal disinfection (10 min, 94° C.), drying phase (15 min).

2. Steam autoclave: fractional preliminary vacuum, sterilization in saturated steam for 18 min at 138° C., (~3414 mbar), drying under vacuum (10 min, ≤120 mbar), cooling to room temperature.

In this Steri-Test, the tested coatings according to the invention with coating parameters according to coating methods 3 and 4 of Example 2 withstood ten cycles consisting of the two mentioned sub-procedures and were thus found to be extremely adhesive.

The invention claimed is:

1. A medical device, comprising on a surface thereof a colored marking in the form of a coating,
wherein the coating, measured by means of X-ray photoelectron spectroscopy (XPS), comprises ≥85 atomic percent (at. %) Ti, O and C, in each case based on the total number of all the atoms of the coating without H;

wherein the coating comprises an amorphous titanium dioxide; and wherein the coating measured by means of XPS, comprises O: from 55.0 at. % to 75 at. %
Ti: from 20 at. % to 44.5 at. %
C: from 0.05 to 15 at. %, in each case based on the total number of all the atoms of the coating without H.

2. The medical device as claimed claim 1, wherein the colored marking in the form of the coating has a layer thickness of from 10 nm to 600 nm.

3. The medical device as claimed in claim 1, wherein the colored marking in the form of the coating has an adhesion such that no detachment occurs in 10 Steri-Test cycles.

4. The medical device as claimed in claim 1, wherein the colored marking in the form of the coating is a CVD layer.

5. The medical device as claimed in claim 1, wherein the colored marking in the form of the coating is applied to only a portion of the surface of the medical device.

6. The medical device as claimed in claim 1, wherein a material of the medical device to which the colored marking in the form of the coating is applied is selected from the group consisting of a steel, a titanium, a magnesium, a titanium alloys, a magnesium alloy, a cobalt-chromium alloy, a polymeric material, a ceramics materials, and a fiber composites.

7. The medical device as claimed in claim 6, wherein the material of the device to which the colored marking in the form of the coating is applied consists of stainless steel.

8. The medical device as claimed in claim 1, wherein the medical device is a medical implant and the medical implant is selected from the group consisting of a screw, a bone nail, a plate, a spinal rod and a Kirschner wire.

9. The medical device as claimed in claim 8, wherein medical implant is an osteosynthesis plate.

10. The medical device of claim 1, wherein the medical device is selected from the group comprising a medical implant and a medical instrument.

11. The medical device of claim 1, wherein the coating measured by means of XPS, comprises C: from 0.1 to 10 at. %.

12. The medical device of claim 1, wherein the coating measured by means of XPS, comprises C: from 0.2 to 5 at. %.

13. The medical device of claim 1, wherein the coating measured by means of XPS, comprises C: from 0.5 at. % to 5 at. %.

14. The medical device of claim 1, wherein the colored marking in the form of the coating has a layer thickness of from 15 nm to 370 nm.

15. The medical device as claimed in claim 1, wherein the material of the medical device to which the colored marking in the form of the coating is applied is selected from the group consisting of a titanium alloy with aluminum, a magnesium alloys with aluminum, a polymeric material, and a ceramic material.

16. The medical device as claimed in claim 15, wherein the polymeric material comprises the polymeric material selected from the group consisting of a PEEK and a composite structure.

17. The medical device as claimed in claim 15, wherein the ceramic material comprises the ceramic material selected from the group consisting of an aluminum oxide and a zirconium oxide.

18. A method for producing a medical device comprising the steps:

a) providing the medical device as a substrate;
b) providing at least one of a Ti-containing metal organic and organometallic precursor;
c) optionally at least one of cleaning, structuring, smoothing and activating the substrate;
d) depositing the precursor onto a surface of the substrate in the presence of a water vapor, thereby forming a coating layer;

wherein the coating layer, measured by means of X-ray photoelectron spectroscopy (XPS), comprises ≥85 atomic percent (at. %) Ti, O and C, in each case based on the total number of all the atoms of the coating layer without H;

wherein the coating layer is in the form of a colored marking on the surface of the substrate; and e) optionally subjecting the coating layer to laser-induced or plasma-induced thermal after-treatment; and wherein the coating measured by means of XPS, comprises O: from 55.0 at. % to 75 at. %
Ti: from 20 at. % to 44.5 at. %
C: from 0.05 to 15 at. %, in each case based on the total number of all the atoms of the coating without H.

19. The method as claimed in claim 18, wherein step d) is carried out under at least one of an atmospheric influence and with an additional infeed of a water.

20. The method as claimed in claim 19, wherein the additional infeed of the water comprises the additional infeed of a water vapor, wherein the water vapor is fed in a liquid volume ratio of the precursor to be vaporized to the water vapor of from 9:1 to 1:100.

21. The method as claimed in claim 18, wherein the precursor is selected from the group consisting of a titanium alkoxide, a titanium organyl, and a titanium phenolate.

22. The method as claimed in claim 21, wherein the titanium alkoxide is a titanium isopropoxide.

23. The method as claimed in claim 18, wherein the step of depositing the precursor is carried out using at least one of at least one nozzle and at least one carrier gas.

* * * * *

UNITED STATES PATENT AND TRADEMARK OFFICE
CERTIFICATE OF CORRECTION

PATENT NO. : 9,968,715 B2
APPLICATION NO. : 14/911077
DATED : May 15, 2018
INVENTOR(S) : Andreas Keil et al.

Page 1 of 1

It is certified that error appears in the above-identified patent and that said Letters Patent is hereby corrected as shown below:

On the Title Page

At (73), delete the Assignee as "FRAUNHOFER-GESELLSCHAFT ZUR FORDERUNG DER ANGEWANDTEN, Munich (DE)" and replace with the Assignee as --Fraunhofer-Gesellschaft zur Förderung der angewandten Forschung e.V., München (DE)--.

In the Claims

Column 21, Line 12, Claim 2: Delete "as claimed claim 1" and replace with --as claimed in claim 1--.

Column 21, Lines 26-27, Line 28 and Lines 28-29, Claim 6: Delete "a titanium alloys" and replace with --a titanium alloy--; delete "a ceramics materials" and replace with --a ceramics material--; and delete "a fiber composites" and replace with --a fiber composite--.

Column 22, Lines 2-3, Claim 15: Delete "a magnesium alloys" and replace with --a magnesium alloy--.

Signed and Sealed this
Ninth Day of July, 2019

Andrei Iancu
*Director of the United States Patent and Trademark Office*